United States Patent
Liu

(10) Patent No.: US 10,932,454 B2
(45) Date of Patent: Mar. 2, 2021

(54) LDL RECEPTOR GENE KNOCKOUT, GENETICALLY-ENGINEERED HAMSTER

(71) Applicant: HEBEI INVIVO BIOTECH INC, Shijiazhuang (CN)

(72) Inventor: Guoqing Liu, Nanjing (CN)

(73) Assignee: HEBEI INVIVO BIOTECH INC, Shijiazhuang (CN)

(*) Notice: Subject to any disclaimer, the term of this patent is extended or adjusted under 35 U.S.C. 154(b) by 219 days.

(21) Appl. No.: 16/074,768

(22) PCT Filed: Feb. 1, 2017

(86) PCT No.: PCT/CN2017/072797
§ 371 (c)(1),
(2) Date: Aug. 1, 2018

(87) PCT Pub. No.: WO2017/133653
PCT Pub. Date: Aug. 10, 2017

(65) Prior Publication Data
US 2019/0037817 A1 Feb. 7, 2019

(30) Foreign Application Priority Data
Feb. 1, 2016 (CN) .......................... 201610069985.2

(51) Int. Cl.
*A01K 67/00* (2006.01)
*A01K 67/027* (2006.01)
*C12N 15/90* (2006.01)
*A61K 49/00* (2006.01)

(52) U.S. Cl.
CPC ...... *A01K 67/0276* (2013.01); *A61K 49/0008* (2013.01); *C12N 15/907* (2013.01); *A01K 2217/075* (2013.01); *A01K 2227/105* (2013.01); *A01K 2267/0362* (2013.01)

(58) Field of Classification Search
CPC .......... A01K 67/0276; A01K 2217/075; A01K 2227/105; A01K 2267/0362
See application file for complete search history.

(56) References Cited

FOREIGN PATENT DOCUMENTS

WO 2017133653 A1 8/2017

OTHER PUBLICATIONS

Fan et al. PLoS ONE 9(10):e109755, 2014. pp. 1-9 (Year: 2014).*
Naito et al. J Reprod Fert 113:137-143, 1998 (Year: 1998).*
Raina et al. Gene 96-100, 2015 (Year: 2015).*
Dolatshad et al. Mammalian Genome 26:598-608, 2015 (Year: 2015).*
Hirose and Ogura Reprod Med Biol. 18:34-39, 2019 (Year: 2019).*
Agellon, L.B. et al. (Jun. 15, 1991). "Reduced High Density Lipoprotein Cholesterol in Human Cholesteryl Ester Transfer Protein Transgenic Mice," J Biol Chem. 266(17):10796-10801.
Bassett, A.R. et al. (Jul. 11, 2013). "Highly Efficient Targeted Mutagenesis of *Drosophila* With the CRISPR/Cas9 System," Cell Rep. 4(1):220-228.
Chang N. et al. (Apr. 2013, e-pub. Mar. 26, 2013). "Genome Editing With RNA-Guided Cas9 Nuclease in Zebrafish Embryos," Cell Res. 23(4):465-472.
Cong, L. et al. (Feb. 15, 2013). "Multiplex Genome Engineering Using CRISPR/Cas Systems," Science 339 (6121):819-823, 9 pages.
Conway, R.S. et al. (Mar. 1994). "Enhanced Coronary Vasoconstriction in the Syrian Myopathic Hamster Supports the Microvascular Spasm Hypothesis," Cardiovasc Res. 28(3):320-324.
De Ferranti, S.D. (Sep.-Oct. 2015, e-pub. May 1, 2015). "Familial Hypercholesterolemia in Children and Adolescents: A Clinical Perspective," J Clin Lipidol. 9(5 Suppl):S11-S19.
Ebihara, H. et al. (Jan. 15, 2015). "A Syrian Golden Hamster Model Recapitulating Ebola Hemorrhagic Fever," J Infect Dis. 207(2):306-318.
Friedland, A.E. et al. (Aug. 2013, e-pub. Jun. 30, 2013). "Heritable Genome Editing in C. elegans Via a CRISPR-Cas9 System," Nat Methods. 10(8):741-743, 13 pages.
Gao, M. et al. (Mar. 2014, e-pub. Jan. 7, 2014). "Generation of Transgenic Golden Syrian Hamsters," Cell Res. 24(3):380-382.
Guillaume, V. et al. (May 10, 2009, e-pub. Mar. 28, 2009). "Acute Hendra Virus Infection: Analysis of the Pathogenesis and Passive Antibody Protection in the Hamster Model," Virology. 387(2):459-465.
Hirano, K.-I. et al. (Jun. 1997). "Cloning and Characterization of the Rat apobec-1 Gene: A Comparative Analysis of Gene Structure and Promoter Usage in Rat and Mouse," J Lipid Res. 38(6):1103-1119.
Hobbs, H.H. et al. (1992). "Molecular Genetics of the LDL Receptor Gene in Familial Hypercholesterolemia," Journal Human Mutation 1(6):445-466.
International Preliminary Report on Patentability, dated Aug. 7, 2018, for PCT Application No. PCT/CN2017/072797, filed Feb. 1, 2017, 5 pages.
International Search Report and Written Opinion, dated May 9, 2017, for PCT Application No. PCT/CN2017/072797, filed Feb. 1, 2017, 23 pages.
Ishibashi, S. et al. (Aug. 1993). "Hypercholesterolemia in Low Density Lipoprotein Receptor Knockout Mice and Its Reversal by Adenovirus-Mediated Gene Delivery," J Clin Invest. 92(2):883-893.
Ishibashi, S. et al. (May 1994). "Massive Xanthomatosis and Atherosclerosis in Cholesterol-Fed Low Density Lipoprotein Receptor-Negative Mice," J Clin Invest. 93(5):1885-1893.

(Continued)

*Primary Examiner* — Marcia S Noble
(74) *Attorney, Agent, or Firm* — Morrison & Foerster LLP

(57) ABSTRACT

Provided is a method for preparing a genetically-engineered hamster comprising in vivo knocking out an LDL receptor gene in the hamster. The LDL receptor gene is knocked out by CRISPR/CAS9 gene editing technique. The genetically-engineered hamster shows significantly high levels of blood lipids, and it thus well-suited for direct use in hyperlipidemia and arteriosclerosis studies, and is a small animal model with high similarities to human familial hypercholesterolemia. Also provided is a method for screening drugs using the genetically-engineered hamster.

10 Claims, 4 Drawing Sheets
Specification includes a Sequence Listing.

(56) References Cited

OTHER PUBLICATIONS

Lee, S.T. et al. (Apr. 2005). "Development of a Hamster Superovulation Program and Adverse Effects of Gonadotropins on Microfilament Formation During Oocyte Development," Fertil Steril. 83(Suppl 1):1264-1274.

Mali, P. et al. (Feb. 15, 2013, e-pub. Jan. 3, 2013). "RNA-Guided Human Genome Engineering Via Cas9," Science 339(6121):823-826, 8 pages.

Nakamuta, M. et al. (May 1998). "Phenotype Interaction of apobec-1 and CETP, LDLR, and ApoE Gene Expression in Mice: Role of ApoB mRNA Editing in Lipoprotein Phenotype Expression," Arteriosclerosis, Thrombosis, and Vascular Biology 18(5):747-755.

Sans-Coma, V. et al. (Jul. 1, 1988). "Origin of the Left Main Coronary Artery From the Pulmonary Trunk in the Syrian Hamster," Am J Cardiol. 62(1):159-161.

Scanu, A.M. et al. (Dec. 1988). "Genetically Determined Hypercholesterolemia in a Rhesus Monkey Family Due to a Deficiency of the LDL Receptor," J Lipid Res. 29(12):1671-1681.

Shiomi, M. et al. (Nov. 2009). "The Watanabe Heritable Hyperlipidemic (WHHL) Rabbit, Its Characteristics and History of Development: A Tribute to the Late Dr. Yoshio Watanabe," Atherosclerosis 207(1):1-7, 16 pages.

Soutar, A.K. et al. (Jun. 1982). "The Metabolism of Very Low Density and Intermediate Density Lipoproteins in Patients With Familial Hypercholesterolaemia," Atherosclerosis 43(2-3):217-231.

Spady, D.K. et al. (1993). "Regulation of Plasma LDL-Cholesterol Levels by Dietary Cholesterol and Fatty Acids," Annu Rev Nutr. Annual Reviews 13(1):355-381.

Takahashi, M. et al. (Feb. 9, 2011). "Experimental Animal Models of Pancreatic Carcinogenesis for Prevention Studies and their Relevance to Human Disease," Cancers (Basel) 3(1):582-602.

Vairaktaris, E. et al. (Apr. 2008, e-pub. Dec. 3, 2007). "The Hamster Model of Sequential Oral Oncogenesis," Oral Oncol. 44(4):315-324.

Van Ree, J.H. et al. (Nov. 1994). "Diet-Induced Hypercholesterolemia and Atherosclerosis in Heterozygous Apolipoprotein E-Deficient Mice," Atherosclerosis 111(1):25-37.

Yokode, M. et al. (Nov. 30, 1990). "Diet-Induced Hypercholesterolemia in Mice: Prevention by Overexpression of LDL Receptors," Science 250(4985):1273-1275.

\* cited by examiner

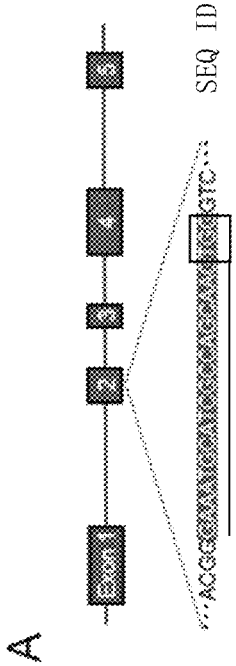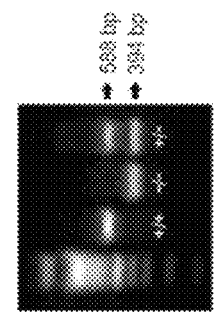
FIG. 1A
FIG. 1B
FIG. 1C

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial sequence
<220> FEATURE:
<223> OTHER INFORMATION: Targeting sequence

<400> SEQUENCE: 1
gaaatgcatc gccagcaag                                                  19

<210> SEQ ID NO 2
<211> LENGTH: 62
<212> TYPE: DNA
<213> ORGANISM: Artificial sequence
<220> FEATURE:
<223> OTHER INFORMATION: Primer

<400> SEQUENCE: 2
gaaattaata cgactcacta taggaaatgc atcgccagca aggttttaga gctagaaata    60
gc                                                                    62
```

```
<210> SEQ ID NO 3
<211> LENGTH: 80
<212> TYPE: DNA
<213> ORGANISM: Artificial sequence
<220> FEATURE:
<223> OTHER INFORMATION: Primer

<400> SEQUENCE: 3
aaaagcaccg actcggtgcc acttttttcaa gttgataacg gactagcctt attttaactt    60
gctatttcta gctctaaaac                                                 80

<210> SEQ ID NO 4
<211> LENGTH: 18
<212> TYPE: DNA
<213> ORGANISM: Artificial sequence
<220> FEATURE:
<223> OTHER INFORMATION: Primer

<400> SEQUENCE: 4
cggcccagat gtcaatat                                                   18

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
gtgaaaccct ccaaaccc                                                   18

<210> SEQ ID NO 6
<211> LENGTH: 29
<212> TYPE: DNA
<213> ORGANISM: Artificial Sequence
<220> FEATURE:
<223> OTHER INFORMATION: Synthetic Construct

<400> SEQUENCE: 6
acgggaaatg catcgccagc aagtgggtc                                       29

<210> SEQ ID NO 7
<211> LENGTH: 40
<212> TYPE: DNA
<213> ORGANISM: Artificial Sequence
<220> FEATURE:
<223> OTHER INFORMATION: Synthetic Construct

<400> SEQUENCE: 7
gcagggacgg gaaatgcatc gccagcaagt gggtctgtga                           40

<210> SEQ ID NO 8
<211> LENGTH: 28
<212> TYPE: DNA
<213> ORGANISM: Artificial Sequence
<220> FEATURE:
<223> OTHER INFORMATION: Synthetic Construct

<400> SEQUENCE: 8
gcagggacgg gaaatgcatc gtctgtga                                        28

<210> SEQ ID NO 9
<211> LENGTH: 30
<212> TYPE: DNA
<213> ORGANISM: Artificial Sequence
```

```
<220> FEATURE:
<223> OTHER INFORMATION: Synthetic Construct

<400> SEQUENCE: 9
gcagggacgg gaaatgcatc gggtctgtga                                              30

<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10
gcagggacgg gaaatgcgtc tgtga                                                   25

<210> SEQ ID NO 11
<211> LENGTH: 35
<212> TYPE: DNA
<213> ORGANISM: Artificial Sequence
<220> FEATURE:
<223> OTHER INFORMATION: Synthetic Construct

<400> SEQUENCE: 11
gcagggacgg gaaatgcatc gccatgggtc tgtga                                        35

<210> SEQ ID NO 12
<211> LENGTH: 40
<212> TYPE: DNA
<213> ORGANISM: Artificial Sequence
<220> FEATURE:
<223> OTHER INFORMATION: Synthetic Construct

<400> SEQUENCE: 12
gcagggacgg gaaatgcatc gccgccaagt gggtctgtga                                   40

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
gcagggacgg gaaatgcatc                                                         20
```

LDL RECEPTOR GENE KNOCKOUT, GENETICALLY-ENGINEERED HAMSTER

CROSS-REFERENCE TO RELATED APPLICATIONS

This application is a U.S. national phase application under 35 U.S.C. § 371 of International Application No. PCT/CN2017/072797, filed on Feb. 1, 2017, which claims priority to CN Application No. 201610069985.2, filed on Feb. 1, 2016, the contents of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792832000100SEQLIST.TXT, date recorded: Aug. 14, 2020, size: 3 KB).

FIELD OF THE INVENTION

The present invention relates to the field of genetically-engineered animal, and more particularly to an LDL receptor gene knockout hamster constructed by CRISPR/CAS9 gene editing technology.

BACKGROUND OF THE INVENTION

Hypercholesterolemia is one of the most important independent risk factors for atherosclerosis and cardiovascular diseases, and it is related to many genetic and environmental factors. Familial hypercholesterolemia is one of the primary hypercholesterolemia. Its pathogenesis is mainly due to mutations in the low-density lipoprotein (LDL) receptor gene, which leads to decreased or lost function, slowed plasma LDL clearance, and elevated cholesterol levels. It results in early onset cardiovascular and cerebrovascular diseases which are often accompanied by skin and tendon xanthomas (1, 2).

Choosing a right animal model for disease is necessary for studying the occurrence, development and outcome of human diseases, for drug screening and for pharmacological research. Because of its small size, rapid reproduction, and low cost, and also because there are various genetically-engineered models, mouse is widely used in experimental research of various diseases. Mouse is not susceptible to atherosclerosis and has not been used in atherosclerosis research until recently. After the advent of apolipoprotein E (apoE) (3) and low-density lipoprotein receptor (LDL-R) knockout mouse (4), mouse quickly became the most commonly used model animal in the field of metabolic cardiovascular disease research. ApoE and LDL-R homozygous KO mice can spontaneously develop atherosclerotic lesions (5), and high-fat diets can accelerate the onset of the lesions. However, because lipid metabolism in mice is quite different from that in humans, and the sensitivity to drugs of mice is also different from that of humans, some research results based on mice are controversial in terms of clinical applications (6). In addition, atherosclerotic lesions in mice occur mostly in the aorta and outflow tract, with minimal involvement of the coronary arteries and cerebral arteries. Therefore, the study of cardio-cerebral vascular complications based on hypercholesteremia in apoE KO and LDL-R KO mice lacks the underlying etiology and pathophysiological basis of coronary artery and cerebral artery diseases, and cannot simulate the natural pathogenesis of human coronary heart disease and stroke, which has obvious drawbacks.

SUMMARY OF THE INVENTION

One aspect of the present invention provides a genetically-engineered hamster, wherein an LDL receptor gene is knocked out in the hamster.

In some embodiments, the hamster is an LDL receptor gene knockout homozygous hamster. In other embodiments, the hamster is an LDL receptor gene knockout heterozygous hamster.

In some embodiments, a blood lipid level of the hamster is significantly increased.

Another aspect of the invention provides a method for preparing a genetically-engineered hamster comprising knocking out an LDL receptor gene in the hamster.

In a preferred embodiment, the LDL receptor gene is knocked out by CRISPR/CAS9 gene editing technology. In some embodiments, an sgRNA sequence employed is a complementary sequence of the hamster LDL receptor gene, targeting the second exon of the LDL receptor gene. For example, in an embodiment, CRISPR-Forward and sgRNA-Reverse sequences employed are set forth in SEQ ID NOs: 2 and 3, respectively.

In some embodiments, the hamster is an LDL receptor gene knockout homozygous hamster. In other embodiments, the hamster is an LDL receptor gene knockout heterozygous hamster.

Another aspect of the present invention provides a method for screening a drug for treatment of cardiovascular disease in humans, comprising the following steps:
a) administering a drug candidate to an LDL receptor gene knockout genetically-engineered hamster,
b) determining a blood lipid level in the genetically-engineered hamster before and after the administration, and
c) if the blood lipid level in the genetically-engineered hamster is significantly decreased after the administration, the drug candidate is determined to be effective.

In some embodiments, the cardiovascular disease may be selected from the group consisting of hyperlipidemia, hypercholesterolemia, and atherosclerosis.

In some embodiments, the blood lipid level may be a blood cholesterol level and/or a triglyceride level.

In some embodiments, the hamster is an LDL receptor gene knockout homozygous hamster. In other embodiments, the hamster is an LDL receptor gene knockout heterozygous hamster.

Another aspect of the present invention provides use of the genetically-engineered hamster in screening a drug for treatment of a cardiovascular disease in humans.

In some embodiments, the cardiovascular disease is selected from the group consisting of hyperlipidemia, hypercholesterolemia, and atherosclerosis.

BRIEF DESCRIPTION OF THE DRAWINGS

FIGS. 1A-1C show the construction of the LDL-R knockout hamster. FIG. 1A: Schematic diagram of the recognition site of the guide RNA on the second exon of the LDL-R gene, wherein the single underlined sequence represents the recognition sequence and the boxed sequence represents the PAM sequence. FIG. 1B: LDL-R gene sequence fragments of two successfully constructed suckling hamsters, wherein the single underlined sequence represents the recognition sequence, the boxed sequence represents the PAM sequence, the double underlined sequence represents the point mutation sequence, the dotted line represents the deletion sequence, and the mutation types are labelled at the end of each line. FIG. 1C: DNA gel electrophoresis pattern of LDL-R deficient Δ194 bp hamster tissue after PCR amplification, DNA length of the deletion fragment was 394 bp.

FIG. 2A: The total cholesterol (left) and triglyceride (right) concentrations in the plasma of the F1 heterozygous hamsters with LDL-R gene bases deletion Δ10 bp, Δ12 bp, Δ14 bp, Δ194 bp and the wild type control hamster on common diet feeding (before) and on high-fat diet feeding (two weeks). FIG. 2B: Distribution of plasma lipoprotein cholesterol in the heterozygous hamster with Δ194 deletion and the wild type control hamster after two weeks of feeding on a common diet (CD) and a high-fat diet (HFD). In the above groups, n=5, and there was a statistically significant difference compared to the wild type control group. (* was P<0.05,  was P<0.01, * was P<0.001).

FIG. 3A: Plasma cholesterol (left) and triglyceride (right) concentrations of normal humans, LDL-R heterozygous deficient and homozygous deficient patients, wild type, LDL-R heterozygous and homozygous mice and hamsters. FIG. 3B: Distributions of plasma lipoprotein cholesterol in normal humans, LDL-R heterozygous deficient and homozygous deficient patients, wild type, LDL-R heterozygous and homozygous mice and hamsters. In the above groups, n=1 for human plasma samples, and n>5 for mouse and hamster plasma samples.

FIG. 4A: Plasma cholesterol (left) and triglyceride (right) concentrations in LDL-R gene deficient Δ194 bp heterozygous hamsters and wild type control hamsters fed on a high-fat diet while being intragastrically administered with 2 mg/kg ezetimibe or distilled water daily for 0 week, 1 week, and 2 weeks. FIG. 4B: The body weight change curve of each group of hamsters in two weeks, the red arrow indicates the time point at which blood was taken after 12 hours of fasting. Plasma lipoprotein cholesterol distributions in LDL-R gene deficient Δ194 bp heterozygous hamsters and wild type control hamsters fed on a high-fat diet while being intragastrically administered with 2 mg/kg ezetimibe or distilled water daily for 2 weeks. In the above groups, n=5, and compared with the group of wild type hamsters with intragastric administration of distilled water, * is P<0.05,  is P<0.01, * is P<0.001; compared with the group of LDL-R gene deficient Δ194 bp heterozygous hamsters with intragastric administration of distilled water, # is P<0.05, ## is P<0.01, and ### is P<0.001.

DETAILED DESCRIPTION OF THE INVENTION

Figures 2A, 2B, 2C:
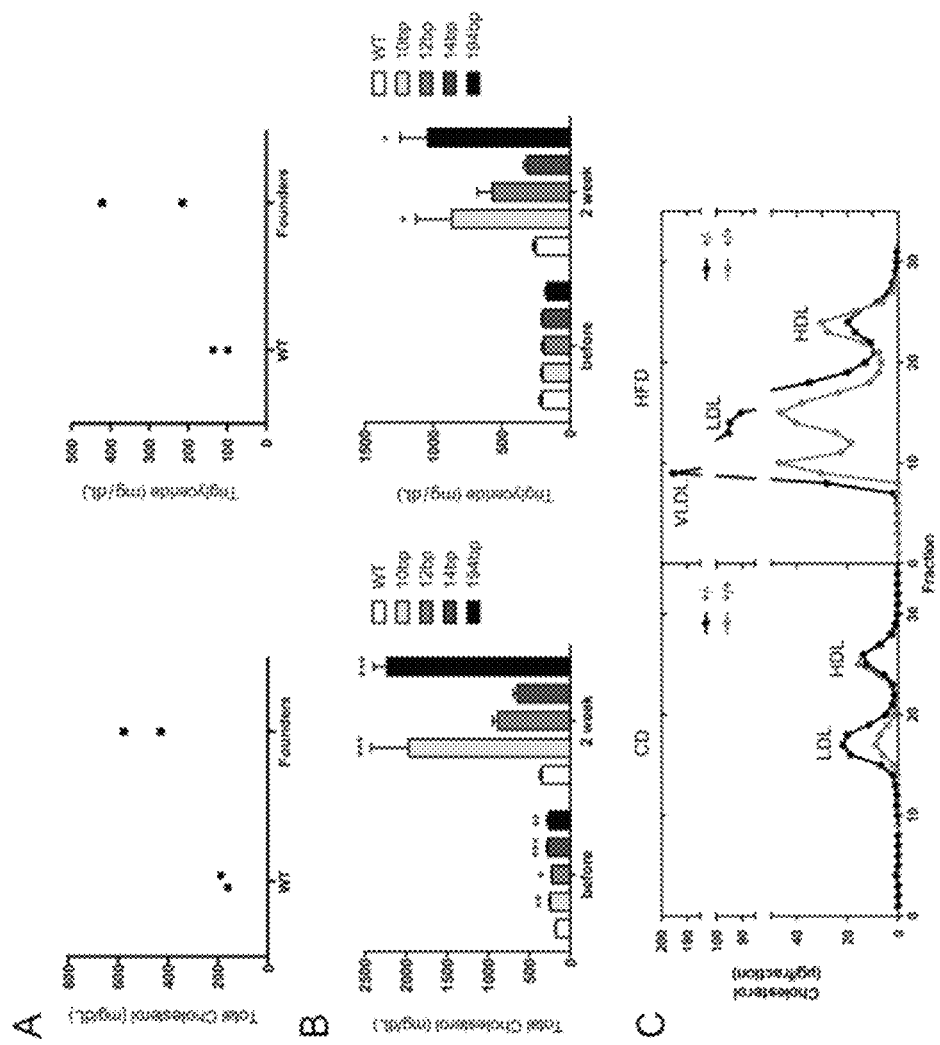
FIGS. 2A-2B show that the F1 generation LDL-R heterozygous hamsters had significant increases in blood lipids and an increase in plasma LDL cholesterol ratio.
FIG. 2C shows results of plasma lipoprotein FPLC analysis.

The term "hamster" as used herein refers to a golden Syrian hamster.

The term "LDL" as used herein refers to a low density lipoprotein.

The term "LDL-R" as used herein refers to a low density lipoprotein receptor. As used herein, the terms "LDL-R", "LDL receptor" and "low density lipoprotein receptor" are used interchangeably.

The term "KO" as used herein refers to gene knockout. For example, "LDL-R KO" means that the low density lipoprotein receptor gene is knocked out.

The term "sgRNA" as used herein refers to a single guide RNA that is complementary to a target gene sequence and directs Cas9 to cleave the target gene.

The term "cardiovascular disease" as used herein generally refers to ischemic or hemorrhagic diseases of the heart, brain and systemic tissues caused by hyperlipidemia, viscous blood, atherosclerosis, hypertension, and the like, including but not limited to hyperlipidemia, hypercholesterolemia, atherosclerosis, and the like.

CRISPR/Cas9 gene editing technique is well known in the art. CRISPR, known as clustered regularly interspaced short palindromic repeats, is actually a gene editor, a system used by bacteria to protect itself against viruses, and a genetic weapon against attackers. Later, researchers found that it appears to be a precise omnipotent genetic weapon that can be used to delete, add, activate, or inhibit target genes in other organisms, and it is a biotechnology that may be widely used.

The CRISPR cluster is a family of specific DNA repeats that are widely found in the genome of bacteria and archaea, with a sequence consists of a leader, a plurality of short and highly conserved repeats, and a plurality of spacers. The leader region is generally located upstream of the CRISPR cluster and is an AT-rich region of 300-500 bp in length, which is considered to be a promoter sequence of the CRISPR cluster. The repeat sequence region has a length of 21 to 48 bp and contains a palindromic sequence, which may form a hairpin structure. The repeat sequences are separated by a spacer of 26 to 72 bp in length. The spacer region consists of captured foreign DNA, similar to immune memory. When foreign DNA containing the same sequence invades, it can be recognized by the bacteria and cut to silence its expression for the purpose of protecting the bacteria themselves.

By analysing the flanking sequence of the CRISPR cluster, it was found that there is a polymorphic family gene in its vicinity. The proteins encoded by this family all contain functional domains (having activities of, such as, nuclease, helicase, integrase, and polymerase) that interact with nucleic acids, and function in conjunction with the CRISPR region, therefore the family was named CRISPR associated, abbreviated as Cas. Currently found Cas includes many types such as Cas1 to Cas10. The Cas gene and CRISPR have evolved together to form a highly conservative system.

When the bacteria resist invasion by foreign DNA such as phage, CRISPR is transcribed into a long RNA precursor (Pre RISPR RNA, pre-crRNA) under the control of the leader region, and then processed into a series of short mature crRNAs containing conserved repeats and spacers that ultimately recognize and bind to their complementary foreign DNA sequence to exert a splicing effect.

There are currently three different types of CRISPR/Cas systems found, namely type I, type II and type III, which are present in approximately 40% of sequenced eubacteria and 90% of sequenced archaea. Wherein the composition of type II is relatively simple, with Cas9 protein and guide RNA (gRNA) as the core composition. Type II is the type that is currently the most studied.

Processing of pre-crRNA in type II system is solely involved by Cas9 in the Cas family. Cas9 contains two unique active sites, RuvC at the amino terminus and HNH in the middle of the protein, which play a role in crRNA maturation and double-strand DNA cleavage. In addition, while pre-crRNA is transcribed, trans-activating crRNA (tracrRNA) complementary to its repeat sequence is also transcribed, and Cas9 and double-stranded RNA-specific RNase III nuclease are activated to process pre-crRNA. After processing to be mature, the crRNA, tracrRNA and Cas9 form a complex that recognizes and binds to the sequence complementary to the crRNA, then unwinds the DNA double strand to form an R-loop, which allows the crRNA to hybridize to the complementary strand, and leaves the other strand in a free single-stranded state. Then the complementary DNA strand of the crRNA is cleaved by the HNH active site in Cas9, and non-complementary strand is cleaved by the RuvC active site, eventually a DNA double strand break (DSB) is introduced. The cleavage site of CRISPR/Cas9 is located in the NGG site in the 5'-GG-N18-NGG-3' characteristic region of the adjacent PAM (Protospacer Adjacent Motif) region downstream of the crRNA complementary sequence, and the characteristic sequence is repeated once every 128 bp of random DNA sequence. The research results show that Cas9 can also cleave linear and supercoiled plasmids with shear efficiency comparable to restriction endonucleases.

Research Overview

Hypercholesterolemia is an important risk factor for cardiovascular and cerebrovascular diseases, and it is related to many other genetic and environmental factors. In the field of biomedical research, animal models used to study hypercholesterolemia are mainly low-density lipoprotein receptor gene knockout (LDL-R KO) and apolipoprotein E gene knockout (ApoE KO) mice. However, the characteristics of blood lipid metabolism, the mechanism of complications such as cardiovascular and cerebrovascular diseases, and the response to drugs in mice are quite different from those in humans, thus the research results have many controversies in clinical applications. In terms of glycolipid metabolism, hamster (Golden syrian hamster) is more similar to human than rat and mouse.

In the previous work, we pioneered the preparation method of genetically-engineered hamster. In this study, we used the CRISPR/CAS9 system in combination with the original patented hamster genetic engineering technology to knock out the hamster LDL-R gene. By measuring the lipid levels of LDL-R heterozygous and homozygous hamsters and comparing them with those of human patients with LDL-R heterozygous and homozygous mutations, the hamster model with LDLR deficiency was found to be highly similar to human familial hypercholesterolemia with significant dominant genetic characteristics. The cholesterol level of the LDL-R heterozygous hamster was significantly higher than that of wild type. After two weeks of feeding on high-fat diet (0.5% cholesterol, 10% fat), the cholesterol level reached 2231 mg/dL, which was 5.5 times of that of a wild type hamster. After administration of the commonly clinically used cholesterol-lowering drug ezetimibe (2 mg/kg), plasma cholesterol was decreased to the level of the wild type hamster fed on common diet, and lipoprotein changes were mainly the decrease of VLDL-C and LDL-C, while HDL-C was not significantly changed. Therefore, unlike the LDLR and ApoE knockout mouse, the LDL-R knockout heterozygous hamsters can be directly used for hyperlipidemia and arteriosclerosis studies, and are a rare animal model that is highly similar to familial hypercholesterolemia in which the human LDL receptor heterozygous gene mutation is dominantly inherited.

EXAMPLES

Example 1

Hamster (golden Syrian hamster) is a small rodent that is widely used in various research areas, including oncology, virology, diabetes, and cardiovascular disease (7-10). In terms of glycolipid metabolism, hamster has characteristics similar to that of human that mouse and rat do not have: highly expressed cholesteryl ester transfer protein (CETP) (11), editing enzymatic activity of apolipoprotein B only in small intestine and high-fat diet induced complex hyperlipidemia (12, 13). Therefore, hamster is likely to become the most ideal small animal model of hyperlipidemia for the study of the pathogenesis and drug efficacy of hyperlipidemia and its complications.

We have recently made a major breakthrough in the technology of hamster embryo manipulation and successfully prepared the first genetically-engineered hamster in the world (14). On this basis, this study used CRISPR/CAS9 gene editing technology (15, 16) to construct LDL-R knockout hamsters, compared their phenotypes with familial hypercholesterolemia patients with LDL-R gene mutation and LDL-R KO mice and conducted analysis.

Experimental Methods and Materials

1. Types and Breeding of Experimental Animals

The wild type hamsters used in the project were from Beijing Vital River Laboratory Animal Technology Co., Ltd., and were kept according to clean grade standards. The temperature was kept at 24° C., humidity at 50-60%, and a light cycle of light from 6:00 to 20:00 and dark from 20:00 to 6:00. All experimental procedures of the knockout hamster model were reviewed by the Experimental Animal Ethics Committee of Peking University.

2. Construction of the CRISPR/Cas9 System 2.1 Design of Hamster LDL Receptor Gene-Specific Targeting Sequences The recognition of the hamster LDL receptor gene-specific targeting DNA sequence was based on the principle of CRISPRE-Cas9 targeting. In the exons of the golden Syrian hamster LDL receptor gene, the sequence of GG(N)18NGG was selected, and BLAST (blast.ncbi.nlm.nih.gov/Blast.cgi) method was applied to perform specificity verification in the whole genome sequences of the golden Syrian hamster. If other genomic sequences were found to exactly match the last 12 bases of the GG(N)18NGG sequence and the PAM sequence, the sequence was considered to have a potential off-target effect, i.e., the target sequence was discarded, and redesigned.

According to the above principle, the targeting sequence in the hamster ldlr gene we employed was gaaatgcatcgccagcaag (SEQ ID NO: 1).

2.2 Preparation of Cas9 mRNA

The cas9 DNA template used in the project was a PXT7 plasmid containing humanized cas9 cDNA (17). PXT7-cas9 has ampicillin resistance and can be used for plasmid amplification; XbaI cleavage site can be used for plasmid linearization.

Prior to transcription, PXT7-cas9 was fully linearized by the action of XbaI. After termination of the reaction, treatment with proteinase K was carried out for 0.5 hours to remove as much RNase as possible from the sample. Further, phenol-chloroform extraction and ethanol precipitation were carried out to obtain a DNA template which can be used for transcription.

The in vitro transcription kit was mMESSAGE mMACHINE T7 kit (Ambion). The transcription system was fully reacted at 37° C. for 2 hours. The cas9 mRNA obtained by the reaction was purified by phenol-chloroform extraction. After isopropanol precipitation, it was dissolved in RNase-free water to a concentration of 500 ng/μl. The size of the obtained mRNA was measured by agarose gel electrophoresis, and the degradation was evaluated. After dispensing, it was stored at −80° C. for injection.

2.3 Preparation of sgRNA (Single-Guide RNA)

The sgRNA template was obtained by amplification of mutual template PCR with the following two synthetic primers with complementary sequences (18). The two sequences synthesized separately were: 1) a specific oligonucleotide sequence CRISPRF, comprising a T7 promoter, an sgRNA sequence and a partial sgRNA backbone portion; 2) a common sequence sgRNA, i.e., the backbone portion.

```
CRISPR-Forward =
                                          (SEQ ID NO: 2)
GAAATTAATACGACTCACTATAGGAAATGCATCGCCAGCAAGGTTTTAGA
GCTAGAAATAGC sgRNA-Reverse =
                                          (SEQ ID NO: 3)
AAAAGCACCGACTCGGTGCCACTTTTTCAAGTTGATAACGGACTAGCCTT
ATTTTAACTTGCTATTICTAGCTCAAAAC
```

The PCR was carried out in a 50 μl system under the conditions of (98° C. for 30 s, 35 cycles of [98° C. for 10 s, 60° C. for 30 s, 72° C. for 15 s], 72° C. for 10 min, 4° C. a). The PCR product was subjected to agarose gel electrophoresis, and a 120 bp DNA band, i.e., a template DNA of sgRNA, was recovered using a gel recovery kit (TAKARA). Treatment with proteinase K was carried out for 0.5 hours to remove as much RNase as possible from the sample. Further, phenol-chloroform extraction and ethanol precipitation were carried out to obtain a DNA template which can be used for transcription.

The in vitro transcription kit was Megascript T7 Kit (Ambion), and the transcription system was fully reacted at 37° C. for 4 hours. The sgRNA mRNA obtained by the reaction was purified by MEGAclear Kit (ambion). it was dissolved in RNase-free water to a concentration of 200 ng/μl. The size of the obtained mRNA was measured by agarose gel electrophoresis, and the degradation was evaluated. After dispensing, it was stored at −80° C. for injection.

3. Construction of Gene Knockout Hamsters 3.1 Collection and Cultivation of Hamster Fertilized Eggs 8-12 weeks old female hamsters were selected to be induced superovulation. The hamster estrus cycle is four days. At 11:00 on the second day of the cycle, i.e., after the estrus symptoms disappeared, 20 IU of pregnant horse serum gonadotropin (PMSG) was injected intraperitoneally. After 82 hours, i.e., in the next cycle of estrus, the female hamsters were caged with the males for mating. 98 hours after PMSG injection, the female hamsters were sacrificed by intraperitoneal injection of an excess amount of sodium pentobarbital. Their fallopian tubes were cut out and placed in pre-warmed M2 medium (Sigma-Aldrich, St. Louis, Mo., USA) at 37° C. Under the dissecting microscope, the swollen ampullar of the fallopian tubes were tom, and the deposit containing fertilized eggs was discharged to collect the fertilized eggs.

The in vitro culture medium of hamster fertilized eggs was HECM-10 (NaCl 113.8 mM, KCl 3 mM, NaHCO$_3$ 25 mM, sodium lactate 4.5 mM, CaCl$_2$) 1 mM, MgCl$_2$ 2 mM, glutamate 0.01 mM, glutamine 0.2 mM, glycine 0.01 mM, histidine 0.01 mM, lysine 0.01 mM, proline 0.01 mM, serine 0.01 mM, asparagine 0.01 mM, aspartate 0.01 mM, cysteine 0.01 mM, taurine 0.5 mM, pantothenate 0.003 mM, PVA 0.1 mg/ml, Sigma-Aldrich) (19). HECM-10 culture droplets were covered with paraffin oil. The culture temperature of the fertilized eggs was 37.5° C., and the CO$_2$ concentration was 10% (14).

3.2 Microinjection

The injection droplets were prepared, and a drop of 100 μl of M2 medium was added to the injection dish, and liquid-sealed with mineral oil. All fertilized eggs left the incubator for less than 15 minutes (20). sgRNA and cas9 mRNA were co-injected into the cytoplasm at injection concentrations of 20 ng/μl and 50 ng/μl, respectively. After the injection, the fertilized eggs were incubated in the incubator for 0.5 hours and then returned to the surrogate mother hamster.

3.3 Fertilized Egg Implantation

Female hamsters with the same age and estrous cycle as the egg-providing hamsters were selected as surrogate hamsters. The surrogate hamsters and the egg-providing hamsters were synchronized and mated with the male hamsters. The next day, the injected fertilized eggs were implanted into the pregnant hamsters from the fallopian tube umbrella. 15 fertilized eggs were implanted in each side of the fallopian tube.

3.4 Genotype Analysis

After the born hamsters were one week old, the toe tissues were taken for DNA extraction and identification. The mutation site was subjected to PCR amplification (ldlr-F=CGGCCCAGATGTCAATAT (SEQ ID NO: 4), ldlr-R=GTGAAACCCTCCAAACCC (SEQ ID NO: 5)), and the obtained products were identified by sequencing. The mutated hamsters were further verified by sequencing: their PCR products were ligated into the pEASY-T1 vector (transgen biotech), and after transformation and culture, a part of the monoclonal was picked for sequencing.

4. High-Fat Diet Feeding and Experimental Treatment of Ezetimibe

The high-fat diet used in the study was a normal rodent diet containing 0.5% cholesterol and 10% lard. The dose of ezetimibe was 2 mg/kg body weight, administered by intragastric administration, and the control group was given tri-distilled water. Plasma was collected before high-fat diet feeding, after two weeks of high-fat diet feeding, before administration and after two weeks of administration, respectively.

The hamsters were fasted for 12 hours at night, anesthetized by intraperitoneal injection of pentobarbital sodium, and about 1 ml of blood was collected from the posterior orbital vein, and heparin was used for anticoagulation.

5. Plasma Lipid Assay

A plasma triglyceride assay kit and a total cholesterol assay kit (Biosino Bio-Technology and Science Inc.) were used to detect plasma triglyceride and total cholesterol levels. High-density lipoprotein cholesterol (HDL-C) was tested for cholesterol levels after removal of apoB-containing lipoproteins by polyethylene glycol precipitation.

The lipid component of plasma lipoprotein was detected by using fast protein liquid chromatography (FPLC) instrument of Amersham Biocsciences, USA, and the plasma lipoprotein fraction was firstly separated by superose 6 HR10/30 column. 200 μl of plasma was loaded through a 0.22 μm syringe filter, and the separated components were automatically collected at a rate of 0.5 mL per minute, 500 μl per component, for a total of 35 components. The above cholesterol detection kit was applied to each component to detect the cholesterol content, and a plasma lipoprotein profile was prepared.

Result

Construction of LDL-R gene mutant hamsters. Using the second exon of the LDL-R gene as a target (FIG. 1A), we designed a guide RNA that specifically recognizes the LDL-R gene. After 120 fertilized eggs were subjected to the cytoplasm injections, they were returned to four pregnant females. A total of 16 pups were born and identified by sequencing after PCR, two of which were LDL-R deficient hamsters. After cas9 endonuclease cleaved at a specific site, the damaged DNA was repaired by direct ligation with its terminal or homologous recombination, resulting in LDL-R mutant chimeric hamsters with many different in vivo genotypes (founders, FIG. 1B). Among them, founder1 and founder2 were chimeras containing four different genotypes, 194 bp large fragment deletions and point mutations, respectively. FIG. 1C shows the results of agarose gel electrophoresis of the F2 generation genotype identification of founder2. The LDL-R knockout hamsters thus established all can be fertile.

Deletion of the LDL-R gene resulted in varying degrees of elevated blood lipids. We analyzed the phenotypes of the founders with different LDL-R gene deletions and the F1 heterozygous and F2 homozygous hamsters.

The founder1 and founder2 constructed in the project were chimeras containing four different genotypes, 194 bp large fragment deletions and point mutations, respectively. At 12th week, plasma cholesterol levels were 578 mg/dL and 429 mg/dL, respectively, and the littermate wild type controls were 189 mg/dL and 161 mg/dL. Triglyceride levels reached 422 mg/dL and 215 mg/dL, significantly higher than triglyceride levels of their littermate WT of 99 mg/dL and 137 mg/dL (FIG. 2A).

Founders mated with WT hamsters to produce heterozygous LDL-R gene mutant hamsters of 6 genotypes. Under normal feed, the levels of LDL-R heterozygous (+/−) Δ194 bp (194 base pairs deletion), Δ10 bp (10 base pairs deletion), and Δ14 bp (14 base pairs deletion) were significantly higher than that of the wild type (WT). After two weeks of high-fat diet feeding, the cholesterol levels of LDL-R+/−Δ194 bp and Δ10 bp reached a maximum of 2231 mg/dL, which was 7.6 times of that before high-fat diet feeding, and 5.5 times of that of high-fat diet feeding WT. The cholesterol levels of LDL-R+/−Δ12 bp, and Δ14 bp reached 881 mg/dL and 645 mg/dL, respectively, which were 2.2 and 1.6 times of that of WT, respectively (FIG. 2B). There were differences in cholesterol levels among different LDL-R+/− genotypes. FIG. 2B shows that the glycerol level of each genotype LDL-R+/− was 190 mg/dL in normal feed, which was not significantly different from WT. After two weeks of high-fat diet feeding, the triglyceride levels of LDL-R+/−Δ194 bp and Δ10 bp reached 1040 mg/dL, which was 4.4 times of that before high-fat diet feeding, and 4.1 times that of high-fat diet feeding WT. Similar to the trend of cholesterol changes, the triglyceride levels of LDL-R+/−Δ12 bp, and Δ14 bp after high-fat diet feeding reached 570 mg/dL and 310 mg/dL, respectively, which were 2.28 and 1.24 times of that of WT, respectively. The following studies mainly focused on hamsters with genotypes of LDL-R+/−Δ194 bp and Δ10 bp for analysis.

The results of plasma lipoprotein FPLC analysis showed (FIG. 2C) that under normal feed, the LDL content of LDL-R+/−Δ194 bp hamster significantly increased compared with that of WT while HDL levels did not change. It is suggested that hamsters have an elevated LDL-C phenotype in the absence of half of the LDL-R gene, which is similar to the dominant genetic feature of clinical familial hypercholesterolemia, that is, heterozygotes have a distinct hypercholesterolemia phenotype. After two weeks of high-fat diet feeding, VLDL and LDL were significantly increased in WT plasma lipids. LDL-R+/− plasma lipids were mainly increased by VLDL and LDL, and HDL levels were not significantly changed.

Figures 3A, 3B:
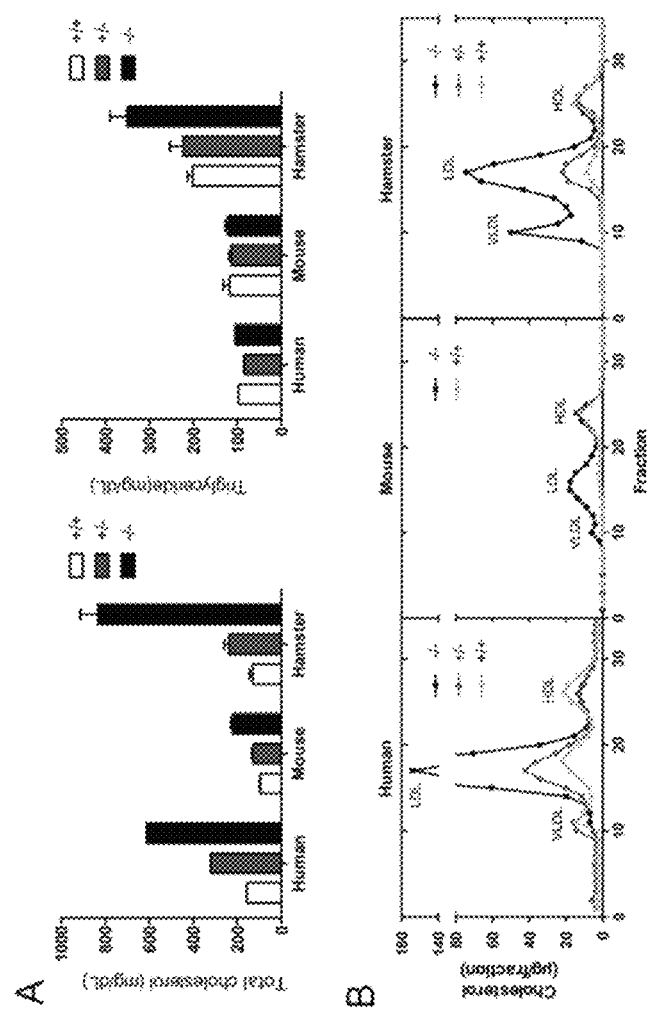
FIGS. 3A-3B show comparisons of blood lipids of LDL-R knockout hamsters with those of humans and mice.

Comparisons of blood lipids of LDL-R knockout hamster with those of human and mouse. To further determine the loss of LDL receptor function, we tested the blood lipids of wild type, heterozygous, and homozygous F2 hamsters. The plasma total cholesterol level of LDL-R knockout homozygous (LDL-R−/−) reached 833 mg/dL, which was 6.4 times of that of the littermate wild type control. The plasma cholesterol level of LDL-R knockout heterozygous (LDL-R+/−) reached 237.8 mg/dL, which was approximately 1.8 times of that of the wild type (FIG. 3A). For comparison with LDL-R−/− hamsters, we collected plasma from a heterozygous patient (26 years old, male) and a homozygous patient (8 years old, male, taking 10 mg statin) with familial hypercholesterolemia, respectively. LDL-R−/− hamsters have cholesterol levels more similar to patients with familial hypercholesterolemia compared to LDL-R gene deficient mouse. Unlike LDL-R deficient mouse and human, the triglyceride level of LDL-R−/− hamster reached 350 mg/dL, which was 1.7 times of that of littermate wild type control hamster (FIG. 3B). The results of FPLC showed that, unlike humans, the main carrier of plasma cholesterol in mice was HDL, with a small amount of LDL and almost no VLDL. In LDL-R+/−, the lipid component was still predominantly HDL, and LDL was almost unchanged (21). LDL levels were only elevated in homozygous LDL-R knockout mice. In the wild type hamsters, there was a certain amount of LDL in the plasma, while in the LDL-R+/− hamsters, the plasma LDL was significantly increased, and the VLDL and HDL were unchanged. The VLDL and LDL of homozygous LDL-R knockout hamsters were both significantly increased.

Figure 4A:
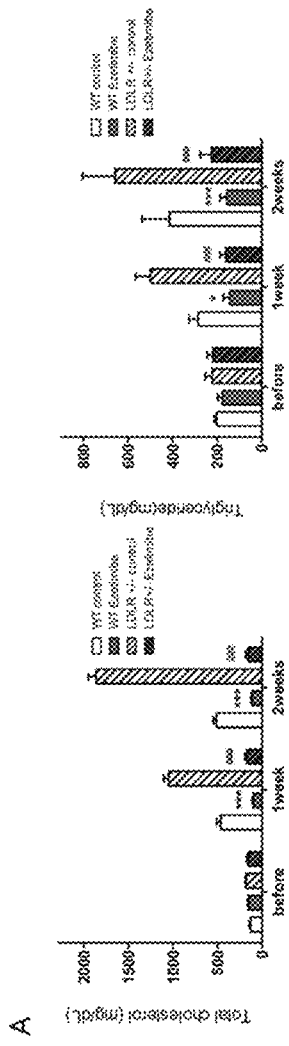
FIGS. 4A-4B show that ezetimibe significantly reverses hyperlipidemia in LDL-R knockout hamsters.
Figure 4B:
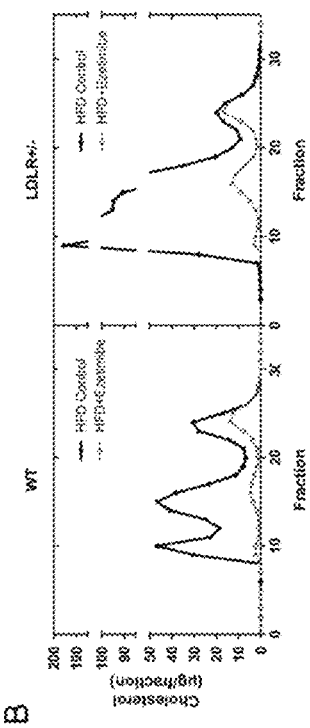

Ezetimibe significantly reversed hypelipidemia of LDL-R knockout hamsters. Hamster is more similar to human in plasma lipid and lipoprotein compositions than mouse. In order to verify whether the commonly used lipid-lowering drugs in clinical practice have the same therapeutic effects on hamsters, we examined changes in plasma lipid and lipoprotein after administration of high-fat diet in LDL-R+/− hamsters followed by administration of ezetimibe. FIG. 4A shows that after high-fat diet feeding in combination with intragastric administration of 2 mg/kg ezetimibe for two weeks, the plasma cholesterol levels of high-fat diet feeding only WT and LDL-R+/− hamsters were 513 mg/dL and 1864 mg/dL, which were decreased to 111 mg/dL and 157 mg/dL, respectively, after administration, close to the levels of common diet feeding. Triglyceride levels were also decreased from 413 mg/dL, 658 mg/dL to 157 mg/dL and 225 mg/dL, respectively. There was no significant difference between the weights of the ezetimibe-administered group and the high-fat diet feeding group. At 7th and 14th days of high-fat diet feeding and administration, body weight was significantly decreased in each group due to fasting and blood withdrawal, and recovered on the next day (FIG. 4B). FPLC results showed that ezetimibe mainly decreased VLDL and LDL in plasma, and had little effect on HDL.

Discussion

In this study, we successfully constructed the LDL-R knockout hamster using the latest genetic editing method CRISPR/CAS9 system. In the traditional gene knockout technique, the strategy of homologous recombination is adopted. However, this method is inefficient and can only be operated on embryonic stem cells, which limits its application to other species other than mouse. With the establishment of high-efficiency gene editing methods such as CRISPR/CAS9 and TALENs, the gene targeting technology has undergone major changes, and its efficiency has been greatly improved. Gene-modified strains can be efficiently obtained at the level of fertilized eggs, greatly expanding the genetically modified species (22). Hamster embryo is extremely sensitive to in vitro manipulation compared to mouse and rat. In the previous work, we made a major breakthrough in the hamster embryo manipulation technology, and first reported the successful preparation of genetically-engineered hamsters in the world (14). Hamsters have characteristics that other rodents do not possess in plasma lipoprotein metabolism and immune responses, but are more similar to humans. Therefore, the birth of genetically-engineered hamsters provides a more ideal animal model for human disease research.

In the construction of LDL-R knockout hamsters, since after the cas9 endonuclease recognizes the specific site and cleave it and the damaged DNA is randomly repaired by direct ligation with its terminal or homologous recombination, hamsters with different degrees of LDL-R gene mutation were produced. We not only obtained an LDL-R knockout hamster with a large fragment of 194 bp deletion, but also an animal model of LDL-R gene deficiency with point mutation and 4 amino acids deletion. In the preliminary lipid analysis, different types of LDL-R+/− hamsters had different elevated cholesterol levels compared to wild type. This is similar to the LDL-R gene polymorphism in patients with hypercholesterolemia, and can be used to study the pathogenesis of patients with different degrees of LDL-R gene deficiency, and provide different clinical treatment strategies.

The known LDL-R gene mutations occur in Watanabe rabbits, macaques, LDL-R knockout mouse, and familial hypercholesterolemia patients in humans (23, 24). Prior to the birth of LDL-R knockout mouse, the model used primarily for hyperlipidemia and atherosclerosis was Watanabe rabbits. Compared with the most commonly used LDL-R knockout mouse, hamster and rabbit have human-like lipid metabolism characteristics: high expression of CETP, sensitive to diet-induced metabolic syndrome, and editing enzymatic activity of apolipoprotein B only in the small intestine (25). Similar to patients with hypercholesterolemia, at 12 months of age, the plasma cholesterol of Watanabe rabbits rose to a very high level of 700 to 1200 mg/dL. However, LDL-R knockout mice caused an extreme increase in plasma cholesterol only under the induction of a high-fat diet. The LDL-R knockout homozygous hamsters constructed in this study reached 833 mg/dL at 6 weeks of age. Similar to human hypercholesterolemia patient, LDL-R mutant hamster is also dominantly inherited, i.e., LDL-R+/− hamster has a hyperlipidemia phenotype. These are features not found in LDL-R and ApoE knockout mice. This means that LDL-R knockout heterozygous hamsters can be used directly for research and represent a large number of clinically heterozygous familial hypercholesterolemia patients (calculated in 1/200, there are 6-7 million patients in China, and there may be more than 30 million in the world). Because the LDL-R gene mutation is dominant inheritance, LDL-R+/− hamsters still have half of the LDL-R function while having a hyperlipidemia phenotype, which can be applied to experimental studies of new drugs, for example, proprotein convertase *Bacillus subtilis* protease kexin-9 (PCSK9) inhibitors, affecting LDL-R function.

In addition, after the selectively breeding, some Watanabe rabbits with severe hypercholesterolemia can have severe coronary artery disease and myocardial infarction. However, the defects of rabbits are in that the pathogenic lipoprotein is O-VLDL, which can be swallowed in a great amount by macrophages without oxidative modification; lack of hepatic lipase, ApoE and ApoAII; and that they are sensitive to cholesterol toxicity as herbivores, so the mechanism of atherosclerosis is different from that of humans. Moreover, due to the difficulty in breeding and the limited number of Watanabe rabbit, it has not been widely used in the field of hypercholesterolemia and atherosclerosis research for several decades. Atherosclerotic lesion in mouse often occurs in the aorta and outflow tract, and rarely involves the coronary artery and cerebral artery. The study of cardio-cerebral vascular complications based on hypercholesterolemia in mouse lacks the underlying etiology and pathophysiological basis of coronary artery and cerebral artery diseases, and cannot simulate the natural pathogenesis of coronary heart disease and stroke in humans, which has obvious drawbacks. It has been reported in the literature (26, 27) that hamster has coronary atherosclerotic lesion after a high-cholesterol diet for 10 months. This suggests that hamster is susceptible to coronary atherosclerosis. In the LDL-R knockout hamster, it is very likely to accelerate the progression of the disease and aggravate the occurrence of the disease, resulting in a natural pathogenesis similar to human coronary heart disease. Therefore, hamster is not only a good small animal model of hypercholesterolemia, but also may be a model animal with atherosclerosis and coronary heart disease and stroke that is more similar to the pathogenesis of human diseases.

REFERENCES

1. Hobbs H H, Brown M S, Goldstein J L. Molecular genetics of the LDL receptor gene in familial hypercholesterolemia. Hum Mutat. Wiley Subscription Services, Inc., A Wiley Company; 1992:1(6):445-66.
2. de Ferranti S D. Familial hypercholesterolemia in children and adolescents: A clinical perspective. J Clin Lipidol. 2015 September; 9(5 Suppl):S11-9.
3. van Ree J H, van den Broek W J, Dahlmans V E, Groot P H, Vidgeon-Hart M, Frants R R, et al. Diet-induced hypercholesterolemia and atherosclerosis in heterozygous apolipoprotein E-deficient mice. Atherosclerosis. 1994 November; 111(1):25-37.
4. Yokode M, Hammer R E, Ishibashi S, Brown M S, Goldstein J L. Diet-induced hypercholesterolemia in mice: prevention by overexpression of LDL receptors. Science. 1990 Nov. 30:250(4985):1273-5.
5. Ishibashi S, Goldstein J L, Brown M S, Herz J, Burns D K. Massive xanthomatosis and atherosclerosis in cholesterol-fed low density lipoprotein receptor-negative mice. J Clin Invest. 1994 May; 93(5):1885-93.
6. Spady D K Woollett L A, Dietschy J M. Regulation of plasma LDL-cholesterol levels by dietary cholesterol and fatty acids. Annu Rev Nutr. Annual Reviews 4139 El Camino Way, P.O. Box 10139, Palo Alto, Calif. 94303-0139, USA: 1993; 13(1):355-81.
7. Ebihara H, Zivcec M, Gardner D, Falzarano D. LaCasse R, Rosenke R, et al. A Syrian golden hamster model recapitulating ebola hemorrhagic fever. J Infect Dis. 2013 Jan. 15; 207(2):306-18.
8. Guillaume V, Wong K T, Looi R Y, Georges-Courbot M-C, Barrot L, Buckland R. et al. Acute Hendra virus infection: Analysis of the pathogenesis and passive antibody protection in the hamster model. Virology. 2009 May 10; 387(2):459-65.

9. Vairaktaris E. Spyridonidou S, Papakosta V. Vylliotis A, Lazaris A. Perrea D, et al. The hamster model of sequential oral oncogenesis. Oral Oncol. 2008 April; 44(4):315-24.
10. Takahashi M, Hori M, Mutoh M, Wakabayashi K, Nakagama H. Experimental animal models of pancreatic carcinogenesis for prevention studies and their relevance to human disease. Cancers (Basel). 2011; 3(1):582-602.
11. Agellon L B, Walsh A, Hayek T. Moulin P. Jiang X C, Shelanski S A, et al. Reduced high density lipoprotein cholesterol in human cholesteryl ester transfer protein transgenic mice. J Biol Chem. 1991 June 15; 266(17): 10796-801.
12. Nakamuta M, Taniguchi S, Ishida B Y, Kobayashi K. Chan L. Phenotype interaction of apobec-1 and CETP, LDLR, and apoE gene expression in mice: role of apoB mRNA editing in lipoprotein phenotype expression. Arteriosclerosis, Thrombosis, and Vascular Biology. 1998 May; 18(5):747-55.
13. Hirano K, Min J, Funahashi T, Davidson N O. Cloning and characterization of the rat apobec-1 gene: a comparative analysis of gene structure and promoter usage in rat and mouse. J Lipid Res. 1997 June; 38(6):1103-19.
14. Gao M, Zhang B. Liu J, Guo X, Li H, Wang T, et al. Generation of transgenic golden Syrian hamsters. Cell Res. 2014 March; 24(3):380-2.
15. Cong L, Ran F A, Cox D, Lin S, Barretto R Habib N, et al. Multiplex genome engineering using CRISPR/Cas systems. Science. American Association for the Advancement of Science; 2013 Feb. 15:339(6121):819-23.
16. Mali P, Yang L, Esvelt K M, Aach J, Guell M, DiCarlo J E, et al. RNA-guided human genome engineering via Cas9. Science. American Association for the Advancement of Science; 2013 Feb. 15; 339(6121):823-6.
17. Chang N, Sun C, Gao L, Zhu D, Xu X, Zhu X, et al. Genome editing with RNA-guided Cas9 nuclease in zebrafish embryos. Cell Res. 2013 April; 23(4):465-72.
18. Bassett A R, Tibbit C. Ponting C P, Liu J-L. Highly efficient targeted mutagenesis of *Drosophila* with the CRISPR/Cas9 system. Cell Rep. 2013 Jul. 11; 4(1):220-8.
19. Lee S T, Kim T M, Cho M Y, Moon S Y, Han J Y, Lim J M. Development of a hamster superovulation program and adverse effects of gonadotropins on microfilament formation during oocyte development. Fertil Steril. 2005 April; 83 Suppl 1(4):1264-74.
20. Fan Z, Li W, Lee S R, Meng Q, Shi B, Bunch T D, et al. Efficient gene targeting in golden Syrian hamsters by the CRISPR/Cas9 system. Tang Y L, editor. PLoS ONE. Public Library of Science: 2014; 9(10):e109755.
21. Ishibashi S, Brown M S, Goldstein J L, Gerard R D, Hammer R E, Herz J. Hypercholesterolemia in low density lipoprotein receptor knockout mice and its reversal by adenovirus-mediated gene delivery. J Clin Invest. 1993 August; 92(2):883-93.
22. Friedland A E, Tzur Y B, Esvelt K M, Colaiácovo M P, Church G M, Calarco J A. Heritable genome editing in *C. elegans* via a CRISPR-Cas9 system. Nat Methods. 2013 August; 10(8):741-3.
23. Soutar A K, Myant N B, Thompson G R. The metabolism of very low density and intermediate density lipoproteins in patients with familial hypercholesterolaemia. Atherosclerosis. 1982 June; 43(2-3):217-31.
24. Scanu A M, Khalil A, Neven L, Tidore M. Dawson G, Pfaffinger D, et al. Genetically determined hypercholesterolemia in a rhesus monkey family due to a deficiency of the LDL receptor. J Lipid Res. 1988 December; 29(12): 1671-81.
25. Shiomi M. Ito T. The Watanabe heritable hyperlipidemic (WHHL) rabbit, its characteristics and history of development: A tribute to the late Dr. Yoshio Watanabe. Atherosclerosis. 2009 November; 207(1):1-7.
26. Conway R S, Natelson B H, Chen W H, Ting W. Enhanced coronary vasoconstriction in the Syrian myopathic hamster supports the microvascular spasm hypothesis. Cardiovasc Res. 1994 March; 28(3):320-4.
27. Sans-Coma V, Arque J M, Durin A C, Cardo M. Origin of the left main coronary artery from the pulmonary trunk in the Syrian hamster. Am J Cardiol. 1988 Jul. 1; 62(1): 159-61.

The invention claimed is:

1. A method for preparing a genetically-engineered hamster comprising:
   (i) introducing a mRNA encoding a sgRNA and a mRNA encoding a CRISPR/Cas9 into a fertilized egg from a hamster, wherein the sgRNA is complementary to a sequence in a hamster LDL receptor gene, and wherein the CRSPR/Cas9 causes a double stranded cleavage in the hamster LDL receptor gene in the genome of the fertilized egg; and
   (ii) implanting the fertilized egg into a surrogate female hamster to provide the genetically-engineered hamster;

wherein the genetically-engineered hamster comprises a deletion and/or point mutation in the hamster LDL receptor gene in the genome, thereby resulting in a knockout of the hamster LDL receptor gene, and wherein the genetically-engineered hamster has an elevated level of a lipid in the blood compared to a wild type hamster.

2. The method of claim 1, wherein hg sgRNA comprises a sequence that is complementary to a sequence of the second exon of the hamster LDL receptor gene.

3. The method of claim 1, wherein the genetically-engineered hamster is heterozygous for the LDL receptor gene knockout.

4. A method for screening a drug for treatment of cardiovascular disease in humans, comprising the following steps:
   a) administering a drug candidate to a hamster, wherein the hamster has a LDL receptor gene knockout in its genome and an elevated level of a lipid in the blood compared to a wildtype hamster,
   b) determining a blood lipid level in the hamster before and after the administration, and
   c) if the blood lipid level in the hamster is significantly decreased after the administration, the drug candidate is determined to be effective.

5. The method of claim 4, wherein the cardiovascular disease is selected from the group consisting of hyperlipidemia, hypercholesterolemia, and atherosclerosis.

6. The method of claim 4, wherein the blood lipid level is a blood cholesterol level and/or a triglyceride level.

7. The method of claim 4, wherein the hamster is heterozygous for the LDL receptor gene knockout.

8. The method of claim 1, wherein the sgRNA comprises a sequence that is complementary to the sequence of SEQ ID NO: 1.

9. The method of claim 5, wherein the blood lipid level is a blood cholesterol level and/or a triglyceride level.

10. The method of claim 5, wherein the hamster is heterozygous for the LDL receptor gene knockout.

\* \* \* \* \*